United States Patent
Brietzke et al.

(10) Patent No.: US 8,496,905 B2
(45) Date of Patent: Jul. 30, 2013

(54) METHOD FOR THE MANUFACTURE OF AN AMMONIUM SULFATE COMPOSITION

(75) Inventors: Stephan Brietzke, Wiesbaden (DE); Peter Groer, Babenhausen (DE); Carl Christoph Mollenkopf, Frankfurt (DE)

(73) Assignee: Nutrinova Nutrition Specialties & Food Ingredients GmbH, Sulzbach (DE)

( * ) Notice: Subject to any disclaimer, the term of this patent is extended or adjusted under 35 U.S.C. 154(b) by 0 days.

(21) Appl. No.: 13/640,330

(22) PCT Filed: Apr. 13, 2011

(86) PCT No.: PCT/EP2011/055791
§ 371 (c)(1),
(2), (4) Date: Dec. 3, 2012

(87) PCT Pub. No.: WO2011/131532
PCT Pub. Date: Oct. 27, 2011

(65) Prior Publication Data
US 2013/0064755 A1 Mar. 14, 2013

(30) Foreign Application Priority Data
Apr. 19, 2010 (EP) ..................... 10160278

(51) Int. Cl.
*C01C 1/242* (2006.01)
(52) U.S. Cl.
USPC .......................................... 423/549
(58) Field of Classification Search
USPC ....................................... 423/549
See application file for complete search history.

(56) References Cited

U.S. PATENT DOCUMENTS

| | | | |
|---|---|---|---|
| 5,084,180 A | 1/1992 | Boateng | |
| 2011/0256045 A1* | 10/2011 | Brietzke et al. | 423/237 |
| 2011/0256046 A1* | 10/2011 | Brietzke et al. | 423/237 |

FOREIGN PATENT DOCUMENTS

| | | |
|---|---|---|
| CN | 1883790 | 12/2006 |
| DE | 3522470 A | 1/1987 |
| DE | 3545196 A1 | 6/1987 |
| DE | 4416571 C1 | 12/1995 |
| DE | 10146689 A | 4/2003 |
| JP | 54-032406 A | 3/1979 |
| WO | WO 2007/079944 A1 | 7/2007 |

OTHER PUBLICATIONS

International Search Report for PCT/EP2011/055791 mailed Nov. 2, 2011.

* cited by examiner

*Primary Examiner* — Timothy Vanoy

(57) ABSTRACT

The present invention describes a method manufacture of an ammonium sulfate composition having a total organic carbon (TOC) content of 1% by weight or less than 1% by weight, based on the total weight of the composition, comprising the following steps:
a) reacting i) waste sulfuric acid comprising an organic tertiary amines with
ii) ammonia in an amount sufficient to obtain a pH of 9.5 or higher
b) separating the organic tertiary amine from the reaction mixture obtained in step a) wherein during the separation the pH of the reaction mixture is maintained at a pH higher than 10 and
c) optionally reducing the content of water and/or other volatile components from the aqueous solution comprising the ammonium sulfate.

11 Claims, 1 Drawing Sheet

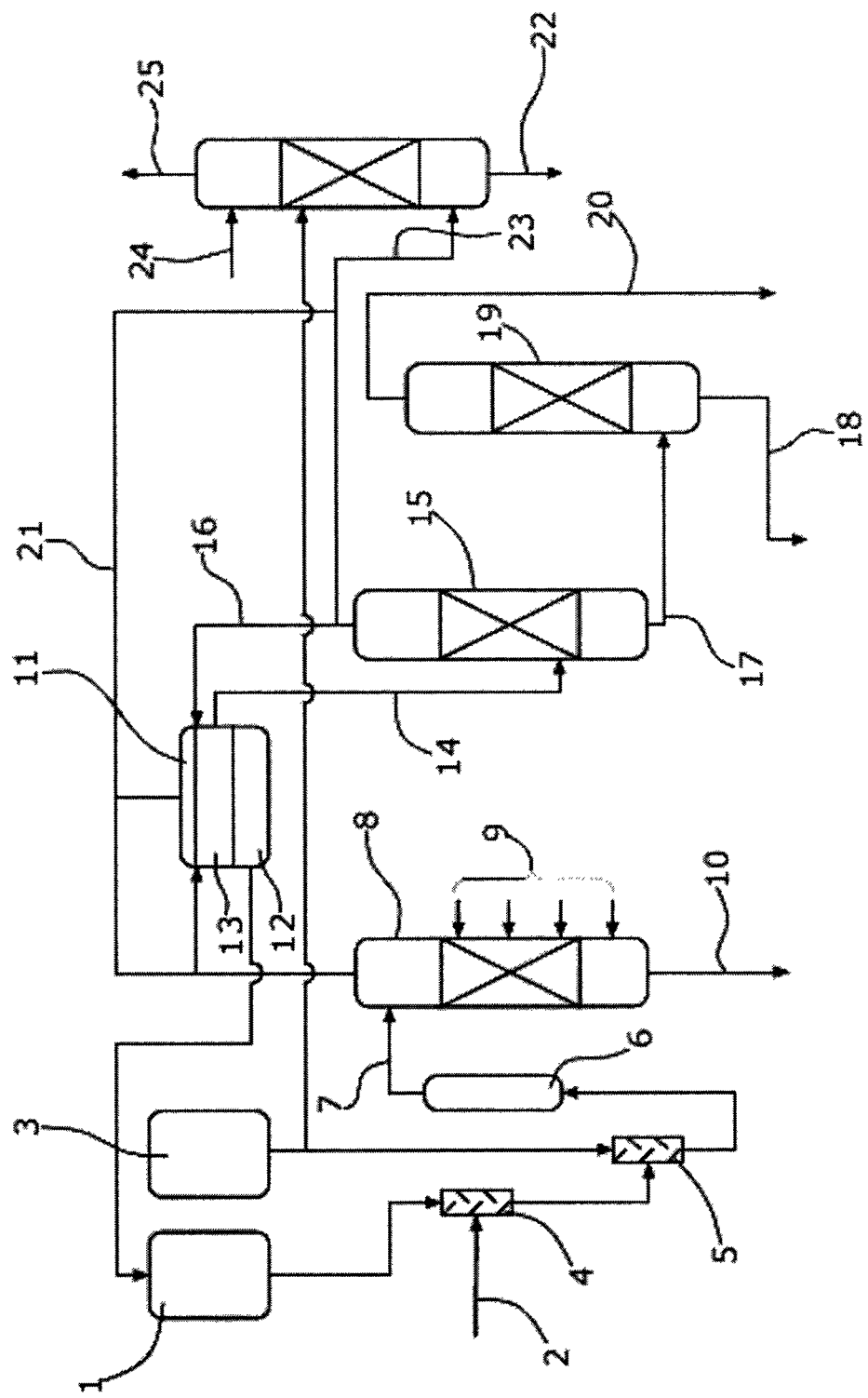

METHOD FOR THE MANUFACTURE OF AN AMMONIUM SULFATE COMPOSITION

This application is a national stage application of PCT/EP2011/055791 filed Apr. 13, 2011, which claims priority to EP Application No. 10160278.7, filed Apr. 19, 2010, the entire contents and disclosures of which are hereby incorporated by reference.

The invention relates to a method for the manufacture of ammonium sulfate having a total organic carbon (TOC) content of less than 1% by weight.

Waste sulfuric acid containing organic tertiary amines is obtained in many chemical plants and is a waste product from various chemical reactions.

The organic tertiary amines do have an economic value and as a consequence, it is desirable to recover the tertiary amines from the waste sulfuric acid. Further, waste sulfuric acid can be converted to ammonium sulfate which is commonly used as a fertilizer. However, it is a requirement for a good inorganic fertilizer that the total amount of organic compounds (TOC) is as low as possible.

DE 35 45 196 A1 discloses a process to recover tertiary aliphatic amines from waste sulfuric acid employing ammonia. However, the yield of the tertiary amines recovered by the process disclosed in DE 35 45 196 A1 is too low and, as a consequence, the total amount of organic compounds which remain in the ammonium sulfate obtained from the process is too high. Thus, the process disclosed in the prior art requires a further purification step in order to reduce the amount of organic compounds in the dry ammonium sulfate to an acceptable level, i.e. a total amount of organic compounds (TOC) of preferably less than 1, more preferably less than 0.5 weight percent based on the dried ammonium sulfate obtained by the process. The TOC is determined in that a sample is oxidized and the amount of generated $CO_2$ is measured. The TOC can be determined according to the standard method DIN EN 1484-H3. Further, for an acceptable fertilizer it is particular important to keep the amount of organic tertiary amine in the ammonium sulfate composition as low as possible. Additionally, the process disclosed in DE 35 45 196 A1 does not recover the economically valuable tertiary amines from the waste sulfuric acid in a sufficient amount.

Therefore, it was an object of the present invention to overcome the problems present in the prior art and in particular, it was an object to significantly increase the yield of tertiary amines recovered from waste sulfuric acid. Further, it was an object to significantly reduce the total amount of organic compounds in the ammonium sulfate obtained from the process to recover the tertiary amine.

It has surprisingly been found that the problems associated with the methods for the manufacture of ammonium sulfate from waste sulfuric acid comprising tertiary amines in the prior art can be solved by a method for the manufacture of ammonium sulfate which uses the reaction of ammonia and waste sulfuric acid and wherein the pH is controlled during the separation process of the tertiary amines.

The invention accordingly provides a method for the manufacture of an ammonium sulfate composition comprising the following steps:
a) reacting i) waste sulfuric acid comprising organic tertiary amines with
   ii) ammonia in an amount sufficient to obtain a pH of 9.5 or higher
b) separating the organic tertiary amine from the reaction mixture obtained in step a) wherein during the separation the pH of the reaction mixture is maintained at a pH higher than 10 and
c) optionally reducing the content of water and/or other volatile components from the aqueous solution comprising the ammonium sulfate.

The ammonium sulfate composition obtained by the method of the present invention preferably has a total organic carbon content (TOC) of 1% by weight or less than 1% by weight, preferably less than 0.8% by weight, especially less than 0.5% by weight, based on the total weight of the composition.

According to a preferred embodiment the amount of total carbon content mentioned above refers to the dried ammonium sulfate obtained by the method of the invention.

Further, preferably the ammonium sulfate composition obtained by the method of the invention comprises at least 99.0% by weight, more preferably at least 99.2% by weight, even more preferably 99.5% by weight ammonium sulfate, wherein the amount is based on the dried composition obtained by the method of the invention.

The total carbon content of the composition obtained by the method of the invention can be determined by usual analytical methods known to the person skilled in the art, according to the standard method DIN EN 1484-H3.

The waste sulfuric acid can in principle comprise all tertiary amines which are suited as organic amines to be recovered from the waste sulfuric acid by the method according to the present invention. The tertiary amines form corresponding hydrogen sulfates (below also referred to as organyl ammonium hydrogen sulfate) with sulfuric acid. Preferred tertiary amines are especially those comprising up to 20 carbon atoms, in particular up to 12 carbon atoms per nitrogen atom. Examples of amines which can be recovered from waste sulfuric acid by the method according to the present invention are selected from the group comprising trimethylamine, triethylamine, diethylpropylamine, tri-n-propylamine, triisopropylamine, ethyldiisopropylamine, tri-n-butylamine, triisobutylamine, tricyclohexylamine, ethyldicyclohexylamine, N,N-dimethylaniline, N,N-diethylaniline, benzyldimethylamine, pyridine, substituted pyridines such as picoline, lutidine, cholidine or methylethylpyridine, N-methylpiperidine, N-ethylpiperidine, N-methylmorpholine, N,N-dimethylpiperazine, 1,5-diazabicyclo[4.3.0]-non-5-en, 1,8-diazabicyclo-[5.4.0]-undec-7-en, 1,4-diazabicyclooctane, tetramethylhexamethylendiamine, tetramethylethylendiamine, tetramethylpropylendiamine, tetramethylbutylendiamine, 1,2-dimorpholylethan, pentamethyldiethyltriamine, pentaethyldiethylentriamine, pentamethyldipropylentriamine, tetramethyldiaminomethane, tetrapropyldiaminomethane, hexamethyltriethylentetramine, hexamethyltripropylenetetramine, diisobutylentriamine and triisopropylentriamine.

Especially preferred is triethylamine.

Ammonia is an inexpensive, easily available chemical basic product and due to its low molecular weight has a highly favorable mass balance.

Ammonia can be used in gaseous or liquid form. According to the invention the partial pressure of the ammonia to be used can be between 0.1 and 300 bar and is limited only by the compressive strength of the used equipment. Ammonia can be used neat or as a mixture with other gases.

Ammonia can be used as a solution in other solvents, preferably as an aqueous solution. The aqueous solution can be obtained commercially or be produced directly from the reaction by introducing gaseous or liquid ammonia in water. The heat of solution can either be removed or retained by transferring the heated solution to the following reaction step. To avoid the exhalation of ammonia it is preferred to work at elevated pressure, e.g. a pressure of higher than 1 bar, preferably 1.5 to 10 bar. In step a) of the method of the present invention, ammonia in gaseous or dissolved form is brought to the reaction with the waste sulfuric acid comprising the organic tertiary amines.

The ammonia is mixed with the waste sulfuric acid in an amount sufficient to obtain a pH of 9.5 or higher. According to a preferred embodiment of the method of the present invention the pH in step a) is preferably ranging from 9.8 to 12, i.e. the ammonia is added to the waste sulfuric acid in an amount sufficient to obtain a pH ranging from 9.8 to 12, more preferably from 10, or higher than 10, to 11.5, especially from 10.1 to 11.5.

During the reaction of the waste sulfuric acid with the ammonia, first the free sulfuric acid is neutralized followed by conversion of organyl ammonium hydrogen sulfate to the corresponding amines. The reaction can be conducted batchwise, e.g. in an agitating machine or continuously in a pump reactor with or without agitation means. In the latter case, a static mixer is also suited, which in turn can be equipped with a temperature equalizer.

In a preferred embodiment of the method according to the present invention the reaction in step a) is conducted in a plug flow reactor. The plug flow reactor is preferred since the reaction can be conducted at elevated pressure and elevated temperature.

The reaction according to step a) of the method of the present invention is preferably conducted at increased pressure, preferably at a pressure ranging from 2 to 12 bar, more preferably from 7 to 10 bar.

The temperature at which the reaction in step a) is conducted is preferably ranging from 95 to 150° C., more preferably from 100 to 140° C., most preferably from 110 to 130° C.

In order to avoid precipitation of ammonium sulfate by exceeding the solubility limit during or after the reaction, water can be added to the reaction mixture. This can be done by diluting the employed waste sulfuric acid with water before the reaction, by adding water during the reaction or by diluting the obtained ammonium sulfate solution after completion of the reaction.

The produced reaction heat can be removed using typical cooling devices known to the person skilled in the art. However, according to a preferred embodiment the released reaction heat of the reaction of step a) is used in separation step b) for the distillative elimination of the organic tertiary amines. In case the reaction in step a) has been conducted under pressure and elevated temperature the expanded reaction mixture can be directly conveyed to the distillation column. Preferably the method is conducted at temperatures which work at the boiling point of the free amine or if present, the boiling temperature of the amine/water azeotrope or above. In case the reaction heat is not sufficient for distillation an additional heating may be required. For example, in the case of triethylamine the preferred temperature is between 75 and 105° C. at 1 bar.

Further, according to a preferred embodiment of the present method, the energy released in step a) is at least partially used to evaporate the water in the concentration process in order to produce the solid ammonium sulfate, i.e. the reaction heat can be used to evaporate the water and/or other volatile components from the aqueous ammonium sulfate solution obtained by the method of the present invention (see step c)).

Preferably an excess of ammonia is mixed with the waste sulfuric acid in order to achieve the required pH of 9.5 or higher.

Solutions which are suitable as waste sulfuric acids contain preferably 0.1 to 100% by weight of the respective organyl ammonium hydrogen sulfate. Solutions may also contain free sulfuric acid and water. A typical waste sulfuric acid can for example, comprise 35% by weight triethylammonium hydrogen sulfate, 45% by weight sulfuric acid, 16% by weight water and minor amounts of organic components.

In step b) of the method of the present invention the organic tertiary amines are separated from the reaction mixture obtained in step a) wherein during the separation the pH of the reaction mixture is adjusted at a pH of higher than 10. Preferably the pH is adjusted to a range from 10.1 to 12, more preferably from 10.2 to 11.5.

The separation of the released amines from the reaction mixture obtained in step a) can be done by distillation, extraction and through phase separation. Distillative separation is especially advantageous for amines with a low boiling point and amines with good water solubility. The above applies especially to amines that form an azeotrope with water. Distillative separation can be done directly from the reaction vessel or in a two stage apparatus.

According to an especially preferred method of the present invention the organic tertiary amine, preferably triethylamine, is separated from the reaction mixture obtained in step a) in a distillation column. According to a preferred embodiment the thermal energy of the products at the still head can be used to heat the feed of the ammonia or the feed of the reaction mixture obtained in step b). In order to maintain a pH of higher than 10 during the separation in a distillation column, ammonia is preferably added to the distillation column. Preferably during the distillation ammonia is added to the distillation column in a counter flow to the reaction mixture obtained in step a).

According to a preferred embodiment, during the distillation the reaction mixture obtained in step a) is continuously fed to the upper part of a distillation column and the ammonia is continuously fed at the lower part or the middle part of the distillation column. The position of the ammonia feed at the distillation column can be used to control the pH of the reaction mixture to be separated during the separation process. The amount of ammonia and consequently the adjusted pH-value influence the capacity of the column with respect to separation of tertiary amines from the aqueous ammonium sulfate solution. The closer the ammonia feed is to the bottom of the distillation column the higher the pH of the reaction mixture in the bottom of the column. The pH value referred to in step b) of the method of the present invention is in case of a separation in a distillation column, the minimum pH value measured in the column between the feed of the reaction mixture and the feed of the ammonia.

Likewise, the position of the ammonia feed at the distillation column also influences the pH value of the aqueous solution comprising ammonium sulfate in the bottom of the column. In a preferred embodiment, the ammonia feed is placed at a position of the distillation column such that the aqueous solution, which is essentially free of the organic tertiary amine, in the lower part of the column has a pH ranging from 5 to 7.

Excess of ammonia can be reintroduced to the process according to the invention. This can be done purposely, e.g. by washing the exhaust containing ammonia with the employed waste sulfuric acid.

According to a preferred embodiment the organic tertiary amine, preferably triethylamine, is recovered in a yield of at least 99.0%, more preferably 99.5%.

The ammonium sulfate solution obtained by the method of the invention represents a quickly recoverable, easily dosable, valuable nitrogen fertilizer. No additional processing is required prior to use. The ammonium sulfate content of the solution can be set as desired by the water content of the used waste sulfuric acid, the addition of water before, during or after the reaction and/or distillative removal of water taking into account the solubility limit of ammonium sulfate in water. In step c) of the method of the invention the content of water and/or other volatile components of the obtained ammonium sulfate composition can be reduced, preferably by distillation of the water or spray drying. Also possible is complete water removal by known methods such as distillation or spray drying, whereby ammonium sulfate is produced as a solid that can be used as a fertilizer.

According to a preferred embodiment, the method of the invention further comprises a dewatering step of the recovered tertiary amine which can optionally be followed by a further distillation of the dewatered amine.

A further embodiment of the present invention is an ammonium sulfate composition which is obtainable by the method of the invention.

The ammonium sulfate composition preferably has a total organic carbon content (TOC) of 1% by weight or less, based on the solid composition, i.e. the water free composition. Preferably, the TOC is less than 0.8% by weight, more preferably less than 0.5% by weight.

The content of ammonium sulfate in the composition is preferably at least 99.0%, more preferably at least 99.5% by weight of the composition. The properties of the ammonium sulfate obtained by the method of the invention are excellent.

The amount of organic tertiary amines in the dried, i.e. water free ammonium sulfate, is preferably less than 0.5% by weight, more preferably less than 0.3% by weight calculated as free tertiary amine based on the ammonium sulfate composition.

A preferred embodiment of the process of the invention is illustrated by means of the following FIG. 1. Figure measures known per se, e.g. addition of stabilizer, are not shown.

FIG. 1 shows a method for the manufacture of ammonium sulfate from waste sulfuric acid comprising triethylamine.

FIG. 1 shows a schematic diagram of a process of the present invention.

| Reference Signs | |
| --- | --- |
| 1 | water reservoir |
| 2 | ammonia supply |
| 3 | waste sulfuric acid reservoir |
| 4 | first plug flow reactor |
| 5 | second plug flow reactor |
| 6 | pipe reactor |
| 7 | feed for the reaction mixture |
| 8 | distillation column |
| 9 | ammonia feed |
| 10 | flow for the ammonium sulfate solution |
| 11 | separator |
| 12 | water phase |
| 13 | organic phase |
| 14 | feed for the organic phase |
| 15 | dewatering column |
| 16 | feed for an azeotrope of water and tertiary amine |
| 17 | flow for the tertiary amine |
| 18 | flow for high boiler |
| 19 | distillation column |
| 20 | flow for the purified tertiary amine |
| 21 | ammonia comprising gases |
| 22 | flow of washing liquid |
| 23 | ammonia supply |
| 24 | water supply |
| 25 | exhaust gas |

Gaseous ammonia is added via ammonia supply (2) to a first plug flow reactor (4) and diluted with water from a water reservoir (1). The aqueous ammonia solution is conveyed to a second plug flow reactor (5) where it is brought into contact with the waste sulfuric acid from the waste sulfuric acid reservoir (3). The waste sulfuric acid and the aqueous ammonia solution are reacted in a pipe reactor (6) and subsequently conveyed to a distillation column (8). The distillation column (8) has different ammonia feeds (9) which can be used to adjust the pH value during the separation process in the column. In the bottom of column (8) the ammonium sulfate solution is obtained which can be released from column (8) by flow (10). The triethylamine-water azeotrope is distilled off and conveyed to the phase separator (11) wherein the azeotrope is separated in a water phase (12) and an organic phase (13) which comprises the triethylamine. The organic phase is fed via feed (14) to the dewatering column (15). The azeotrope of water and triethylamine distilled off in the dewatering column (15) is conveyed via feed (16) to the separator (11). The triethylamine obtained at the bottom of dewatering column (15) is conveyed via flow (17) to distillation column (19). In distillation column (19) the purified triethylamine is distilled off via flow (20). From the bottom of distillation column (19) high boiling organic residues can be separated via flow (18). Ammonia containing gases are conveyed via line (21) and (23) to a column with a flow (22) and a water supply (24) and a supply from the waste sulfuric acid reservoir (3). Exhaust gas which is essentially free from ammonia can be released from the column via line (25).

The ammonia containing washing liquid released via flow (22) can be reintroduced in the process.

Separation of Triethylamine in a Distillation Column 195 g of ammonia mixed with 755 g of water is reacted with 900 g of waste sulfuric acid consisting of 148 g water, 400 g $H_2SO_4$ and 334 g triethylammoniumhydrogensulfate (equivalent to 171 g of triethylamine) and additional 700 g of water.

The reaction mixture exhibits a pH value of 10. Subsequently, the reaction mixture is fed to the upper part of a distillation column while at the lower part of the distillation column ammonia is fed to the column in a counter flow fashion in order to keep the pH of the reaction mixture above 10. The pH value of the mixture in the column can be adjusted by the position of the ammonia feed at the lower part of the column.

Different pH values have been adjusted and the amount of triethylamine recovered has been determined. The weight-% of triethylamine recovered is based on the total weight of triethylamine present in the waste sulfuric acid.

TABLE 1

Example 1 and Comparative Examples 2 to 5

| Example | pH-value determined during separation | weight-% of triethylamine recovered |
| --- | --- | --- |
| 1 (according to the invention) | 10.1 | 99.0 |
| 2 (comparative) | 9.5 | 93.0 |
| 3 (comparative) | 9.0 | 68.0 |
| 4 (comparative) | 7.0 | 2.0 |
| 5 (comparative example 2 of DE 35 45 196) | not mentioned | 92.6% |

The amount of free triethylamine based on the solid ammonium sulfate has been calculated for Example 1 and Comparative Example 5.

For Example 1, 2190 mg/kg and for Comparative Example 5, 7522 mg/kg of free triethylamine based on the dried ammonium sulfate has been calculated. This demonstrates that the method according to the invention leads to the production of ammonium sulfate with a significantly reduced amount of organic tertiary amines. The ammonium sulfate composition of the invention does not need to be further purified prior to its use as a fertilizer.

The invention claimed is:

1. Method for the manufacture of an ammonium sulfate composition comprising the following steps:
   a) reacting i) waste sulfuric acid comprising an organic tertiary amines with
      ii) ammonia in an amount sufficient to obtain a pH of 9.5 or higher and
   b) separating the organic tertiary amine from the reaction mixture obtained in step a) to form an aqueous solution comprising the ammonium sulfate and an organic tertiary amine stream;
      wherein during the separation the pH of the reaction mixture is maintained at a pH of higher than 10.

2. Method according to claim 1 wherein the organic tertiary amine is separated. from the reaction mixture obtained in step a) in a distillation column.

3. Method according to claim 2 wherein during the distillation ammonia is added to the distillation column.

4. Method according to claim 3 wherein during the distillation ammonia is added to the distillation column in a counter flow to the reaction mixture obtained in step a).

5. Method according to claim 4 wherein during the distillation the reaction mixture obtained in step a) is continuously fed to the upper part of a distillation column and the ammonia is continuously fed to the lower part or the middle part of the distillation column.

6. Method according to claim 5 wherein the ammonia feed is placed at a position of the distillation column such that the aqueous solution, which is essentially free of organic tertiary amine and which comprises the ammonium sulfate, in the lower part of the column has a pH ranging from 5 to 7.

7. Method according to claim 1 wherein the organic tertiary amine is triethylamine.

8. Method according to claim 1 wherein the aqueous solution, which is essentially free of the organic tertiary amine and which comprises the ammonium sulfate, is adjusted to a pH ranging from 5 to 7.

9. Method according to claim 1 wherein in step c) the water content and/or the content of volatile components is reduced by distillation or spray drying.

10. Ammonium sulfate composition obtainable by a method according to claim 1.

11. Method according to claim 1, further comprising the step of:
    reducing the content of water and/or other volatile components from the aqueous solution comprising the ammonium sulfate.

* * * * *